United States Patent
Findl et al.

(10) Patent No.: US 10,987,213 B2
(45) Date of Patent: Apr. 27, 2021

(54) METHOD FOR SELECTING AN IOL ON THE BASIS OF THE PREDICTION OF THE ANATOMICAL, POST-OPERATIVE POSITION AND ORIENTATION THEREOF

(71) Applicant: Carl Zeiss Meditec AG, Jena (DE)

(72) Inventors: Oliver Findl, Vienna (AT); Michael Trost, Stadtroda (DE); Nino Hirnschall, Vienna (AT); Martin Volkwardt, Stadtroda (DE); Ferid Bajramovic, Mamming (DE); Tanja Teuber, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 28 days.

(21) Appl. No.: 16/061,919

(22) PCT Filed: Dec. 16, 2016

(86) PCT No.: PCT/EP2016/081482
§ 371 (c)(1),
(2) Date: Jun. 13, 2018

(87) PCT Pub. No.: WO2017/103145
PCT Pub. Date: Jun. 22, 2017

(65) Prior Publication Data
US 2018/0368970 A1  Dec. 27, 2018

(30) Foreign Application Priority Data
Dec. 17, 2015 (DE) ............ 10 2015 225 759.2

(51) Int. Cl.
*A61F 2/16* (2006.01)
*A61B 3/00* (2006.01)
*G16H 50/50* (2018.01)

(52) U.S. Cl.
CPC .............. *A61F 2/16* (2013.01); *A61B 3/0025* (2013.01); *A61F 2240/002* (2013.01); *G16H 50/50* (2018.01)

(58) Field of Classification Search
CPC .... A61F 2/16; A61F 2240/002; A61B 3/0025; A61B 3/1005; A61B 34/10;
(Continued)

(56) References Cited

U.S. PATENT DOCUMENTS

| 5,968,095 A | 10/1999 | Norrby |
| 2011/0052020 A1* | 3/2011 | Hildebrand .......... A61B 3/0025 382/128 |
| 2013/0345807 A1 | 12/2013 | Olsen |
| 2014/0111765 A1 | 4/2014 | Deboer |
| 2016/0302660 A1* | 10/2016 | Buhren ................ A61B 3/1005 |

FOREIGN PATENT DOCUMENTS

| DE | 10 2011 106 714 A1 | 1/2013 |
| DE | 11 2013 002 998 T5 | 3/2015 |
| WO | WO 2010/109020 A1 | 9/2010 |
| WO | WO 2012/120080 A1 | 9/2012 |

OTHER PUBLICATIONS

PCT International Search Report and Written Opinion for International Application No. PCT/EP2016/081482, dated Mar. 10, 2017, 12 pages.
(Continued)

*Primary Examiner* — Jennifer Dieterle
*Assistant Examiner* — Tiffany P Shipmon
(74) *Attorney, Agent, or Firm* — Patterson Thuente Pedersen, P. A.

(57) ABSTRACT

Knowledge of the anatomical, post-operative position and orientation influences not only the selection of the IOL to be implanted but also the result of the refractive operation on the eye. In the method for selecting an IOL to be implanted into an eye on the basis of the prediction of the anatomical, post-operative position (ALP) and orientation thereof, based on pre-operative measuring values such as, for example,
(Continued)

| Location parameter of the IOL (target values) | Predictors according to the invention | Prediction model(s) |
|---|---|---|
| Axial position (ALP) | Curvature of the natural lens $K_V$, $K_R$ | $ALP = f(ACD, LD) + a1 * K_V + a2 * K_R$<br><br>$f(ACD, LD)$ corresponds to the above-mentioned prediction model |
| Decentration (dx, dy) | Decentration natural lens dxl, dyl | $dx = b1 + b2 * dxl$<br>$dy = c1 + c2 * dyl$ |
| Tilting ([nx,ny,nz]) | tilting of the natural lens [nxl, nyl, nzl] | $nx = d1 + d2 * nxl$<br>$ny = e1 + e2 * nyl$<br>$nz = f1 + f2 * nzl$ | anterior chamber depth (VKT), lens thickness (LD) and axial eye length (AL), the invention additionally or exclusively uses the curvature(s) of the eye lens or measuring values derived therefrom. The proposed method is used to predict the anatomical, post-operative position (ALP) and orientation of an intraocular lens (IOL) to be implanted into an eye.

14 Claims, 3 Drawing Sheets

(58) Field of Classification Search
CPC ....... A61B 5/0082; A61B 5/1072; A61B 8/08; A61B 8/0858; A61B 8/10; A61B 3/103
See application file for complete search history.

(56) References Cited

OTHER PUBLICATIONS

English translation of International Search Report for International Application No. PCT/EP2016/081482, dated Mar. 10, 2017, 2 pages.
DE Search Report for 10 2015 225 759.2, dated Aug. 8, 2016, 9 pages.
English translation of International Report on Patentability for PCT International Search Report and Written Opinion for International Application No. PCT/EP2016/081482, dated Jun. 28, 2018, 4 pages.

* cited by examiner

| Location parameter of the IOL (target values) | Predictors according to the invention | Prediction model(s) |
|---|---|---|
| Axial position (ALP) | Curvature of the natural lens $K_V$, $K_R$ | ALP = f(ACD, LD) + a1 * $K_V$ + a2 * $K_R$<br><br>f(ACD, LD) corresponds to the above-mentioned prediction model |
| Decentration (dx, dy) | Decentration natural lens dxl, dyl | dx = b1 + b2 * dxl<br>dy = c1 + c2 * dyl |
| Tilting ( [nx,ny,nz]) | tilting of the natural lens [nxl, nyl, nzl] | nx = d1 + d2 * nxl<br>ny = e1 + e2 * nyl<br>nz = f1 + f2 * nzl |

FIG. 1

METHOD FOR SELECTING AN IOL ON THE BASIS OF THE PREDICTION OF THE ANATOMICAL, POST-OPERATIVE POSITION AND ORIENTATION THEREOF

RELATED APPLICATIONS

This application is a National Phase entry of PCT Application No. PCT/EP2016/081482 filed Dec. 16, 2016 which application claims the benefit of priority to German Application No. 10 2015 225 759.2, the entire disclosures of which are incorporated herein by reference.

FIELD OF THE INVENTION

Embodiments of the present invention relate to a method for selecting an intraocular lens (IOL) that is implanted in an eye. The selection is based on the prediction of its anatomical, post-operative position and orientation thereof. Such a prediction plays a significant role, since this understanding has a significant influence on the selection of the IOL that is to be implanted and thus also on the result of the refractive eye surgery.

BACKGROUND

According to the prior art, solutions for the prediction of the position at which an intraocular lens stabilizes after a refractive eye surgery can be divided into two categories.

Commonly, nowadays the first category-forming, formula-based method, a prediction of the anatomical, post-operative position of an IOL is not carried out in the actual sense.

Rather, the formula-based methods for the prediction of a post-operative lens position are carried out based on various assumptions which are based on the different biometric parameters of the eye. Only a virtual analysis parameter is predicted, which is conceptually derived from an IOL position, which however was generated by application of an optimization of a constant. The hereby determined, formula-specific lens position is also referred to as post-operative, effective lens position (ELP), and should not be confused with an actual, post-operative lens position.

In connection with the well-known methods for the prediction or determination of the post-operative ELP, there is the negative effect, that none of the known methods can be carried out without empirical correction factors. One reason for this are individual, post-operative healing processes, which last for a period of several weeks and which are not considered in previous methods. Another reason can be found in the fact, that despite a vast array of methods, only an insufficient amount is considered for the determination of the ELP-relevant parameters in the prediction.

Another problem is found in the optimization method for improving the post-operative refraction results in which the consideration of individual error sources is not included.

In contrast to this, it is attempted to predict the anatomical, post-operative position (ALP) of the IOL in the second category, which also corresponds to the actual post-operative position on the optical axis of the eye.

Although pre-operatively available measuring values are required for the determination of both values, the results of the determination are fundamentally different. While the predictor for the ELP is based on the subjective refraction after the surgery, it is based on the actually measured IOL position for the ALP, which is required for further methods, such as e.g. the ray tracing.

The term ray tracing refers, as it can already be derived from the terms to a method for tracing the ray. It is known that objects around us can only be perceived by us, because these are illuminated by a light source and because these light rays are reflected by them, of which some rays eventually reach our eyes. The ray tracing method simulates this elementary natural phenomenon. If the optical system, i.e. the individual human eye with all its optical elements, is known, then it is possible to calculate a "real" image, which is appearing on the retina by application of ray tracing. The method is thus based on a detailed eye model by using the corneal topography of the eye.

The U.S. Pat. No. 5,968,095 A describes a method for the pre-operative selection of an IOL that is to be implanted into an eye. One step of the method includes the determination of the position of the haptic lens level of the eye, in which the IOL is to be attached. The determination of the position of the haptic lens level can thereby be carried out either by application of ultrasound bio-microscopy, as well as by means of optical coherence tomography or microscopy or also by application of Scheimpflug photography. After the determination of further parameters such as the refractive strength of the cornea and the axial length, other eligible IOLs that are to be implanted are calculated in dependence of the desired post-operative refractive strength, and the IOL design that is to be used is selected. By application of this method it is thus possible to predict the ALP of the implanted IOL independent of the individual IOL design.

The WO 2012/120080 A1 also describes a method for predicting the post-operative position of an implanted IOL, in which the position and thickness of the existing crystalline lens is determined pre-operatively and an individual numeric constant C is calculated from this information, to predict the post-operative position of the implanted IOL. Next to the IOL type and the patient type, information regarding one or more individuals who had eye surgery is included into the calculation of the constant C. The invention is based on the assumption, that an IOL will localize at a defined position that is dependent on the position and thickness of the crystalline lens in the pre-operative eye. The ALP of the implanted IOL is predicted based on this assumption.

The method described in the DE10 2011 106 714 A1 is also used for the pre-operative selection of an intraocular lens that is to be implanted into an eye, wherein the result of the refractive surgery at the eye is to be optimized by application of a prediction of the post-operative, anatomical position of the implanted IOL. In the herein described method, the post-operative lens position is predicted based on known measuring values such as the cornea thickness, the anterior chamber depth, the length of the eye as well as the distances of the capsular bag equator or of the lens haptic with reference to the front surface of the lens. In addition to the anatomical, post-operative position of the intraocular lens that is to be implanted, its position is also included hereby into the calculation, by application of which additional parameters of the pseudophakic eye are used, which had not been considered before. The suggested method is suitable for a more accurate prediction of the strength and type of an intraocular lens, which is to be implanted into the pseudo phakic eyes in the course of a surgical cataract or refractive surgery. The method is hereby based on the use of suitable calculation methods such as e.g. geometrical-optical formulas or the ray tracing.

SUMMARY OF THE INVENTION

Example embodiments of the present invention are based on removing the disadvantages of the known solutions according to the prior art and to optimize the selection of an IOL that is to be implanted into an eye based on the prediction of its anatomical, post-operative lens position (ALP).

Embodiments of the method according to the invention for selecting an intraocular lens (IOL) that is to be transplanted into an eye based on the prediction of its anatomical, post-operative position (ALP) and orientation based on pre-operative measuring values such as e.g. the anterior chamber depth (VKT), lens thickness (LD) and eye length (AL), and it is solved in that the curvature(s) of the eye lens or measurements that are derived thereof are used additionally or exclusively.

The suggested method is used for selecting an intraocular lens (IOL) that is to be transplanted into an eye, based on the prediction of its anatomical, post-operative position (ALP) and orientation thereof. In contrast to methods that only determine a virtual position of the IOL, the actual post-operative position and orientation of an IOL is being described with the method according to the invention, which e.g. is absolutely required for further methods such as the ray tracing.

BRIEF DESCRIPTION OF THE DRAWINGS

The invention will be described in more detail by means of embodiments in the following. It is shown:

FIG. 1: is a tabular list of possible prediction models.

DETAILED DESCRIPTION

Figure 2:
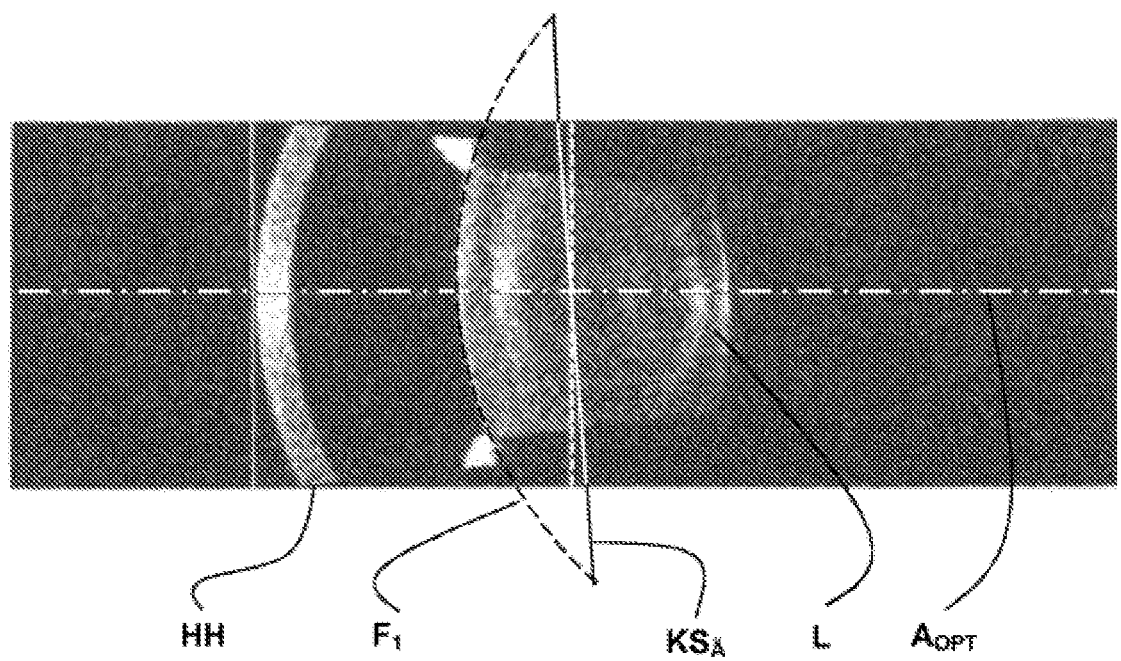
FIG. 2: depicts a function that is adapted to the curvature of the front surface of the eye lens for determining the orientation of the capsular bag equator.

In the method for selecting an IOL that is to be transplanted into an eye based on the prediction of its anatomical, post-operative position (ALP) and orientation based on pre-operative measuring values such as e.g. the anterior chamber depth (VKT), lens thickness (LD) and eye length (AL), the curvature(s) of the eye lens or measuring values that are derived thereof are used additionally or exclusively in accordance with the invention. Since the prediction of the anatomical, post-operative position (ALP) is based on the fact, that the transplanted IOL with its haptic comes to rest within the capsular bag equator, the orientation of the capsular bag equator and/or the measuring values that correlate with it are determined in accordance with the invention. The anatomical, post-operative position (ALP) is hereby understood to be the distance between the front surface of the cornea and the haptic plane of the IOL.

The suggested method for selecting an IOL that is to be transplanted into an eye is based on a prediction of its anatomical, post-operative position (ALP) and orientation thereof, which is as accurate as possible. According to the invention, pre-operative measurable information of the natural eye lens is hereby used, which correlate with the anatomical, post-operative position (ALP) and orientation of the implanted IOL.

The prediction is based on a mathematical relation in the form of a so-called "prediction model". The term prediction is hereby understood to be the prediction by application will of scientific generalization. The variables used for the prediction of a characteristic are called "predictors". In the suggested method, additional prediction coefficients are used, which need to be determined empirically.

For illustrative purposes, it is referred to a known "prediction model". Also in this case, the target value is the anatomical, post-operative position (ALP) of the IOL, which corresponds to the following mathematical relation:

$$ALP = a1 + a2*ACD + a3*LD$$

In this case the cornea thickness (ACD) and the lens thickness (LD) are the predictors and a1, a2 and a3 are the prediction coefficients.

FIG. 1 shows a tabular list of possible prediction models in this regard.

According to the invention, possible predictors of the natural lens are:

its curvatures ($K_V$, $K_R$),
its decentration (dxl, dyl) and
its tilting (described as normal vector) [nxl, nyl, nzl].

The herein described prediction models in accordance with the invention belong to the class of (multi-) linear regression methods. However, it is also possible to use other methods of the regression analysis, with prediction models that are to be described in a correspondingly different mathematical manner.

In accordance with a first example embodiment, the curvature of the front surface of the eye lens is detected along various meridians as further pre-operative measuring value and the orientation of the capsular bag equator is determined on the optical axis of the eye or by application of measuring values that correlate to this. According to the invention, the detection of the curvature of the surface of the eye lens is carried out along, for example, at least 3, in another example 6, in a further example more than 18 different meridians. The determination of the orientation of the capsular bag equator on the optical axis of the eye or of a measuring value that correlates to this is carried out for each meridian with the aid of at least one pre-operative measuring value, example the lens thickness (LD). An average value can be formed from the measuring values that had been determined for the individual meridians, wherein so-called outliers are preferably not considered when generating the average value. The accuracy of the orientation of the capsular bag equator on the optical axis of the eye or of a measuring value that correlates with this can thus be improved considerably by application of this procedure.

FIG. 1 depicts a scan of a real eye, in which the eye lens L and the cornea HH can be seen. A function $F_1$ is attached to the curvature of the front surface of the eye lens L for the determining of the orientation of the capsular bag equator $KS_{\bar{A}}$. The orientation of the capsular bag equator $KS_{\bar{A}}$ is characterized by means of the intersection point with the optical axis $A_{OPT}$.

Corresponding to a second example embodiment, the orientation, i.e. the tilting and/or the decentration of the front surface of the eye lens in relation to the optical axis of the eye is additionally detected in that the front surface is completed by means of interpolating, that it is extrapolated by application of adapting of functions and that the orientation of the plane that is spanned by the capsular bag equator is determined with reference to the optical axis of the eye or by means of measuring values that correlate to it.

In this case, the determination of the orientation of the plane that is spanned by the capsular bag equator is also carried out with the aid of at least one pre-operative measuring value, preferably the lens thickness (LD).

While the tilting of the plane that is spanned by the capsular bag equator in relation to the optical axis of the eye can be determined in a simple manner, additional mathematical calculations are necessary for the determination of its decentration.

It is e.g. possible to use the focal point of the plane that is spanned by the capsular bag equator to determine the decentration. But it is also possible to view the entire ball segment-like shape, raise a perpendicular at the highest point of the curvatures and use the intersection point with the plane that is spanned by the capsular bag equator to determine the decentration. Principally it is also possible to use pre-operative measuring values for the determination of the decentration.

According to a third example embodiment, the curvatures of both, the front as well as the rear surface of the eye lens are detected, both curvatures are extrapolated to be intersected by application of adapting of functions. The intersection point of the straight line through the intersection points of both curvatures with the optical axis then corresponds to the orientation of the capsular bag equator or to a measuring value that correlates to it. According to the invention, the detection of the curvatures of the front and rear surface is also carried out along for example, at least 3, in another example 6, in a further example more than 18 different meridians in this case.

No further pre-operative measuring value is hereby required for the determination of the orientation of the capsular bag equator on the optical axis of the eye or of a measuring value that correlates with it.

In this embodiment of the method, an average value can also be formed from the measuring values that were determined for the individual meridians, wherein so-called outliers are for example not considered when generating the average value. The accuracy of the orientation of the capsular bag equator on the optical axis of the eye or of a measuring value that correlates with this can thus be improved considerably by application of this procedure.

FIG. 2 also depicts a scan of a real eye, in which the eye lens L and the cornea HH can be seen. The functions $F_1$ and $F_2$ are adapted to the curvatures of the front and rear surface of the eye lens L for the determining of the orientation of the capsular bag equator $KS_{\bar{A}}$. The capsular bag equator $KS_{\bar{A}}$ is characterized by a straight line through the intersection points of both curvatures $F_1$ and $F_2$ and by its position due to the intersection point of this straight line with the optical axis $A_{OPT}$.

Corresponding to a fourth example embodiment, the orientation, i.e. the tilting and/or the decentration of the front and/or rear surface of the eye lens in relation to the optical axis of the eye, are additionally detected, the curvatures are completed to curvature surfaces by interpolating, they are extrapolated by adapting of functions so that they will intersect. The section plane that results thereof corresponds to the position of the plane stretched out by the capsule bag equator or by the measuring values which correlate to it with reference to the optical axis.

In this case, no further pre-operative measuring value is required for the determination of the position of the plane stretched out by the capsule bag equator with reference to the optical axis of the eye.

With regard to the determination of the tilting or decentration of the plane stretched out by the capsule bag equator, reference is made to the second advantageous embodiment.

In line with the invention, the determination of the orientation of the capsule bag equator or of the position of the plane stretched out by the capsule bag equator or by measuring values correlating to it, is carried out for all embodiments of the method in such a way, that the detected curvature(s) of the surface(s) of the eye lens can be brought into a relation exclusively or by application of further post-operatively determined measuring values with reference to the position and/or orientation of the implanted IOL and that they can then be generalized as a function.

In accordance with the invention, the relation between the detected curvature(s) of the surface(s) of the eye lens and the determined position and/or orientation of the capsular bag equator or of measuring values correlating to it, corresponds to a linear function in the shape of $f(x)=mx+n$.

Figure 4:
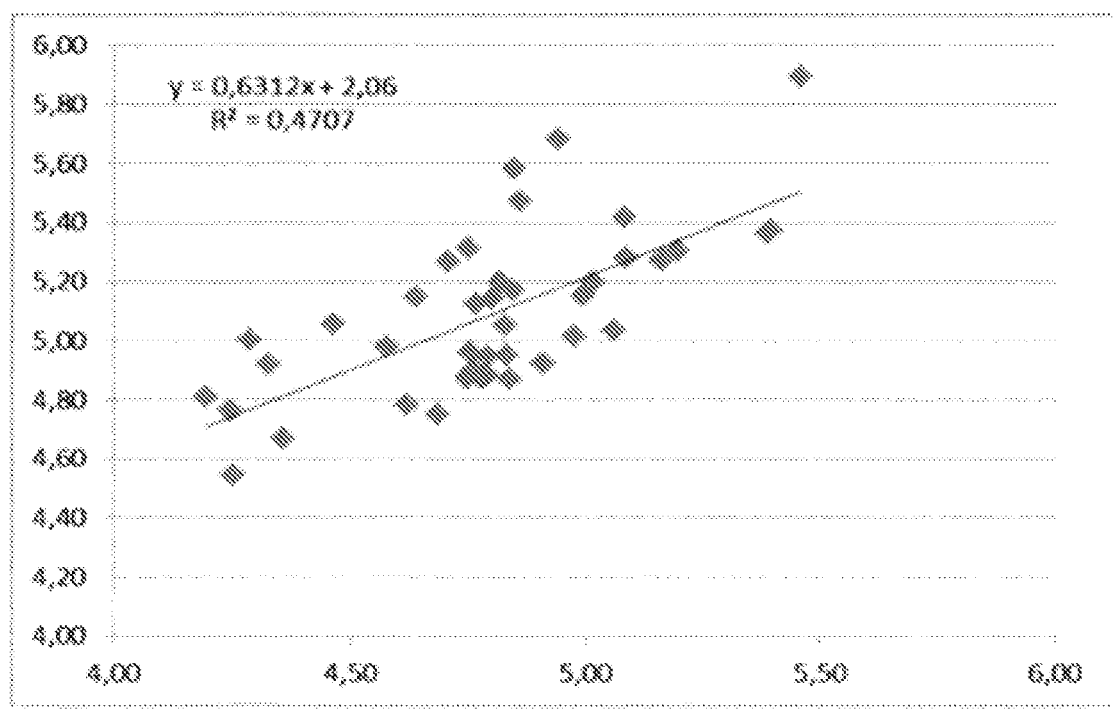
FIG. 4: the correlation of the capsular bag equator, which was determined based on the curvature of the front and rear surface, with the anatomical, post-operative position of the IOL that is to be transplanted
Figure 5:
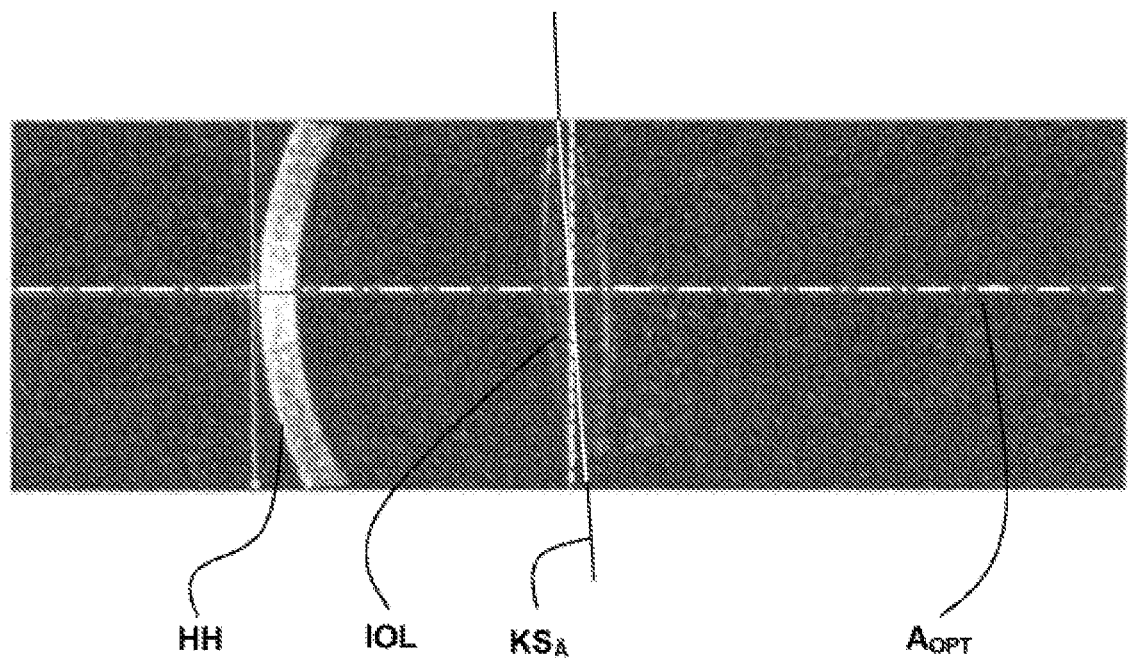
FIG. 5: the anatomical, post-operative position of an IOL that is to be implanted within the capsular bag equator.

In this regard, FIG. 4 depicts the correlation of the capsular bag equator, which was determined by means of the curvature of the front and rear surface, with the anatomical, post-operative position of the transplanted intraocular lens.

The anatomical, post-operative positions of transplanted intraocular lenses are plotted on the abscissa of the coordinate system and the determined orientation of the capsular bag equator on the ordinate. It can be derived from the entered measuring values that the co-relation of a linear function follows the shape of $f(x)=mx+n$.

In line with this invention, a method is provided, by which it is possible to predict with great accuracy the anatomical, post-operative position (ALP) and orientation of an IOL that is to be transplanted into an eye on the basis of pre-operative measuring values. An exact prediction is particularly possible in that the transplanted intraocular lens (IOL) with its haptic comes to rest within the capsular bag equator.

Figure 3:
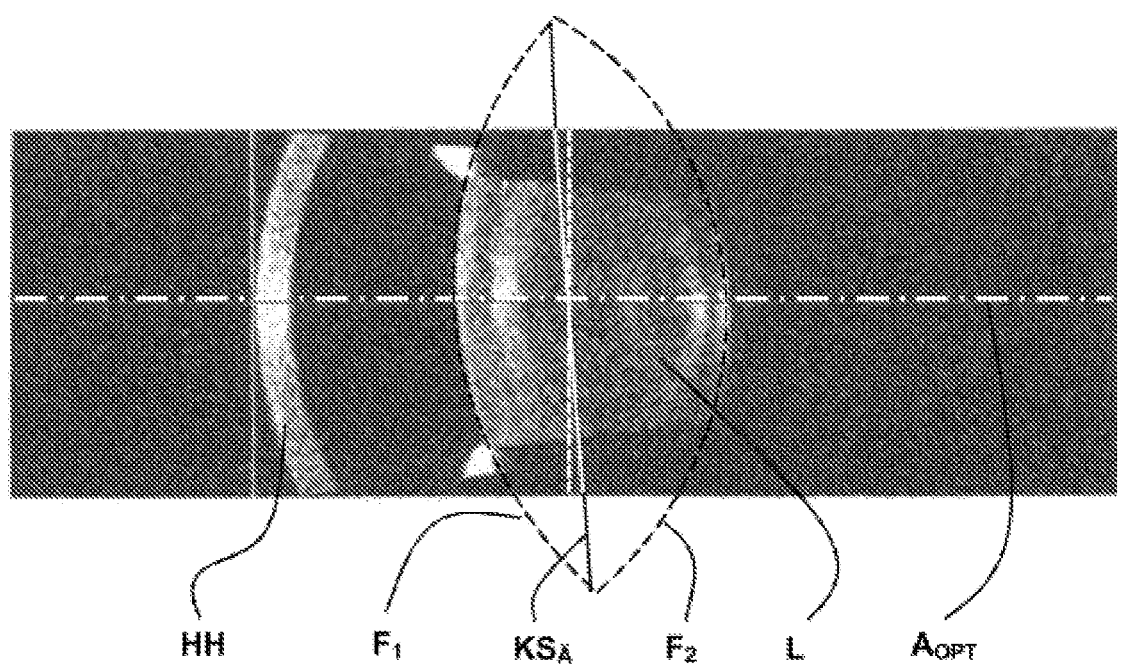
FIG. 3: depicts a function that is adapted to the front and rear surface of the eye lens for determining the orientation of the capsular bag equator.

FIG. 3 also depicts the scan of a real eye. However, the cornea HH and the intraocular lens IOL can be seen herein. In the depiction, the capsular bag equator $KS_A$ is shown in addition to the optical axis $A_{OPT}$. It can thus be derived from the depiction, that the intraocular lens IOL with its haptic comes to rest within the capsular bag equator $KS_A$.

The particular advantage of the method according to the invention can be seen in that dilation of the pupil is not necessary, by which the burden on the patient can be reduced.

Thus, for the definition of a predictor for the prediction of the anatomical, post-operative position ALP and orientation, it is necessary to use such pre-operative measuring values that correlate to the post-operative positions of the IOL, such as e.g. corneal thickness (ACD), lens thickness (LD), eye length (AL), or even the curvature of the natural eye lens or of measuring values that are derived thereof.

The invention claimed is:

1. A method for selecting an intraocular lens (IOL) that is to be implanted into an eye comprising:
   measuring the eye pre-operatively to determine values selected from a group consisting of anterior chamber depth (VKT), lens thickness (LD) and eye axial length (AL) and a combination of the foregoing;
   basing a prediction of an anatomical, post-operative position (ALP) of the IOL and orientation of the IOL on a prediction model utilizing the pre-operative measuring values selected from the group consisting of the anterior chamber depth (VKT), the lens thickness (LD) and the eye axial length (AL) and the combination of the foregoing;

using a curvature or curvatures of a crystalline lens or the measuring values that are additionally or exclusively derived from the curvature or curvatures of the crystalline lens as part of the prediction model; and prescribing or implanting the selected intraocular lens (IOL) based on the prediction.

2. The method according to claim 1, further comprising basing the prediction of the anatomical, post-operative position (ALP) on a presence of a haptic of the implanted intraocular lens (IOL) within a capsular bag proximate a capsular bag equator, and correspondingly determining an orientation of the capsular bag equator and/or measuring values that correlate with the capsular bag equator in accordance with the presence of the haptic of the implanted intraocular lens (IOL) within the capsular bag proximate the capsular bag equator.

3. The method according to claim 2, further comprising detecting a curvature of a front surface of the crystalline lens as a further pre-operative measuring value and determining the orientation of the capsular bag equator on the optical axis of the eye or by measuring values that correlate to the orientation of the capsular bag equator.

4. The method according to claim 3, further comprising carrying out the detecting of the curvature of the front surface of the crystalline lens along different meridians.

5. The method according to claim 4, further comprising carrying out the detection of the curvature(s) of the surface(s) of the crystalline lens along a number of different meridians selected from a group consisting of at least 3, 6 or more than 18 different meridians.

6. The method according to claim 3, further comprising additionally detecting tilting or decentration or both of the front surface of the crystalline lens in relation to the optical axis of the eye, completing curvatures to a curvature surface by interpolating, extrapolating tilting or the decentration or both of the front surface of the crystalline lens by an adapting of functions and determining an orientation of a plane that is spanned by the capsular bag equator with reference to an optical axis of the eye or by correlating measuring values.

7. The method according to claim 6, further comprising carrying out the detection of the curvatures of both the front as well as the rear surface of the crystalline lens along different meridians.

8. The method according to claim 7, further comprising carrying out the detection of the curvature(s) of the surface(s) of the crystalline lens along a number of different meridians selected from a group consisting of at least 3, 6 or more than 18 different meridians.

9. The method according to claim 3, further comprising carrying out the determining of the position and/or orientation of the capsule bag equator or of measuring values that are correlating to orientation of the capsule bag equator in such a way that the detected curvature(s) of the surface(s) of the crystalline lens are brought into a relation with post-operatively determined measuring values with reference to the position and/or orientation of the implanted IOL and that the detected curvature(s) are then generalized as a function.

10. The method according to claim 9, wherein a relation between the detected curvature(s) of the surface(s) of the crystalline lens and of the determined position and/or orientation of the capsular bag equator or of measuring values correlating to it corresponds to a linear function in the shape of $f(x)=mx+n$.

11. The method according claim 3, wherein predicting of the post-operative positions of the IOL is based on a relation between post operatively determined measuring values with reference to position and/or orientation of the implanted IOL and the preoperatively determined position or orientation of the capsular bag equator, the relation corresponding to a linear function in the shape of $f(x)=mx+n$.

12. The method according to claim 1, further comprising detecting curvatures of both a front as well as a rear surface of the crystalline lens, and extrapolating both curvatures of the front and rear surface of the crystalline lens to intersect by adapting of functions and wherein an intersection point of a straight line through the intersection point of both curvatures with the optical axis corresponds to the orientation of the capsular bag equator or with a measuring value that is correlating thereto.

13. The method according to claim 12, further comprising detecting the tilting, the decentration or both of the front surface, rear surface or both of the crystalline lens in relation to the optical axis of the eye, completing the curvatures to curvature surfaces by interpolating, extrapolating the curvatures so that the curvatures intersect by an adapting of functions and wherein the resulting section plane corresponds to the orientation of the plane that is spanned by the capsular bag equator or to measuring values that are correlating to the capsular bag equator with reference to the optical axis.

14. The method according to claim 12, further comprising carrying out determination of the position and/or orientation of the capsule bag equator or of measuring values that are correlating to orientation of the capsule bag equator in such a way that the detected curvature(s) of the surface(s) of the crystalline lens are brought into a relation with post-operatively determined measuring values with reference to the position and/or orientation of the implanted IOL and that the detected curvature(s) are then generalized as a function.

* * * * *